United States Patent [19]

Mawhinney et al.

[11] Patent Number: 4,753,243
[45] Date of Patent: Jun. 28, 1988

[54] PULSE RATE MONITOR

[75] Inventors: Daniel D. Mawhinney, Livingston Township, Essex County; Henry F. Milgazo, Brick Township, Ocean County, both of N.J.

[73] Assignee: RCA Corporation, Princeton, N.J.

[21] Appl. No.: 3,167

[22] Filed: Jan. 14, 1987

[51] Int. Cl.$^4$ .............................................. A61B 5/02
[52] U.S. Cl. ..................... 128/687; 128/661; 128/663; 128/653
[58] Field of Search ............... 128/633, 662, 687, 653, 128/661, 663

[56] References Cited

U.S. PATENT DOCUMENTS

| | | | |
|---|---|---|---|
| 3,176,681 | 4/1965 | Smith | 128/687 |
| 3,187,098 | 6/1965 | Farrar et al. | 128/687 |
| 3,189,023 | 6/1965 | Salz et al. | 128/687 |
| 3,605,723 | 9/1971 | King et al. | 128/662 |
| 3,742,938 | 7/1973 | Stern | 128/687 |
| 3,851,320 | 11/1974 | Dahl | 340/189 M |
| 4,182,315 | 7/1977 | Vas et al. | 128/687 |
| 4,216,462 | 8/1980 | McGrath et al. | 128/904 |
| 4,307,728 | 12/1981 | Walton | 128/687 |
| 4,344,440 | 8/1982 | Aaby et al. | 128/653 |
| 4,513,748 | 4/1985 | Nowogrodzki et al. | 128/687 |

Primary Examiner—William E. Kamm
Assistant Examiner—Timothy Keegan
Attorney, Agent, or Firm—Henry I. Steckler; Donald S. Cohen; Joseph S. Tripoli

[57] ABSTRACT

A pulse rate monitor comprises first and second units coupled by a cable. The first unit has a microwave ocillator that provides a pulsating DC signal in accordance with the pulse rate to the second unit which amplifies the signal. Since the first unit does not comprise microwave components other than the oscillator, it can be miniturized. The second unit also supplies power to the first unit.

8 Claims, 1 Drawing Sheet

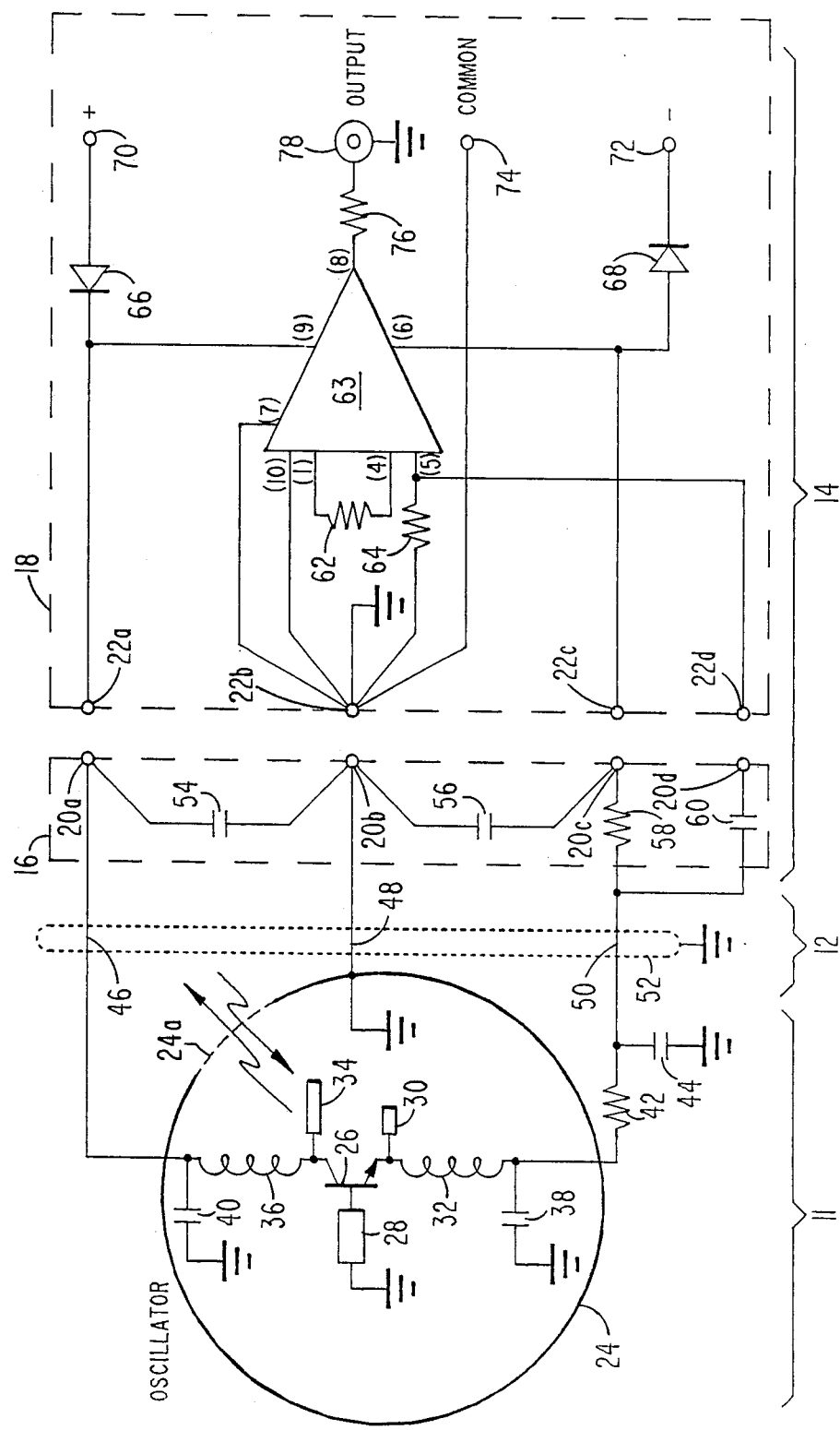

PULSE RATE MONITOR

The Government has rights in this invention pursuant to Subcontract No. 44277 under Contract No. F33615-81-C-0500 awarded by the Department of the Air Force.

BACKGROUND OF THE INVENTION

The present invention relates to pulse rate monitors, and more particularly, to a superficial temporal artery (STA) monitor that can be miniturized.

One type of prior art STA monitor uses a microwave Doppler radar system to detect motion of the artery. The system comprises an oscillator, a directional coupler, a circulator, a mixer, and an I.F. amplifer. Since all of these components, except for the I.F. amplifier, operate at microwave frequencies, they must be placed close together to avoid attenuation, spurious signal pick up, noise, and phase changes caused by any interconnecting cable, and any motion thereof, conveying microwave signals. Thus all of the components, except for the I.F. amplifier, must be disposed near the subject to ensure sufficient coupling thereto to obtain a reliable pulse rate signal. The result is a bulky monitor that cannot be easily placed in a restricted volume, e.g., a helmet.

It is, therefore, desirable to provide a miniturized pulse rate monitor.

SUMMARY OF THE INVENTION

An apparatus for monitoring the pulse rate of a subject comprises a first unit means having an oscillator adapted to be proximate said subject, said unit means providing a pulsating DC signal in accordance with the pulse rate of said subject; a cable coupled to said first unit means to transmit said pulsating DC signal; and a second unit means adapted to be placed distant from said subject and coupled to said cable for receiving and amplifying said pulsating DC signal.

Since the first unit means comprises only an oscillator that provides a pulsating DC signal, it can be readily miniturized.

DESCRIPTION OF THE DRAWING

The sole FIGURE is a schematic diagram of an embodiment of the invention.

DETAILED DESCRIPTION OF THE PREFERRED EMBODIMENT

The invention comprises a first unit means 11 for providing a pulsating DC signal in accordance with the pulse rate of a subject, such as a human, and located proximate the subject, a cable 12 for conveying the signal, and a second unit means 14 for receiving and amplifying the pulsating DC signal, which can be conveniently located. Although not necessary to obtain a sufficient signal, the first unit means 11 preferrably contacts the subject to eliminate relative motion therebetween. Similarly, it has been found convenient to have the second unit means 14 comprise a first portion disposed in a female connector 16 having pins 20 and a second portion disposed in a male connector 18 having pins 22. Pins with identical letter suffixes mate together to form electrical connections therebetween, respectively.

The first unit means 11 comprises an oscillator conveniently and substantially disposed in a grounded case 24, such as type TO-3, having a dielectric covered opening 24a, providing a signal at about 2450±50 Mhz. The oscillator comprises a transistor 26, such as Type HXTR 4103, manufactured by Hewlett-Packard Co., Palo Alto, Calif., having a base coupled to a microstrip line 28 of approximately one-quarter wavelength long at the operating frequency, an emitter coupled to a pad 30 to provide feedback capacitance and a choke 32, and a collector coupled to an antenna 34 and a choke 36. The chokes 32 and 36 are bypassed to ground by capacitors 38 and 40, respectively. A resistor 42 (about 50 ohms) and a bypass capacitor 44 (about 0.01 $\mu$F) are located next to the case 24 to prevent spurious low frequency oscillations.

The cable 12 comprises a first wire 46 conveying a positive voltage connected to the pin 20a, a grounded second wire 48 connected to the pin 20b, a third wire 50 conveying a negative voltage and a pulsating DC signal representing the pulse rate of the subject, and a grounded shield 52 to reduce interference.

The first portion of the second unit means 14 comprises a pair of line filter capacitors 54 and 56 (about 10 $\mu$F) respectively coupled between pins 20a and 20b, and 20b and 20c. A current limiting and voltage sensing resistor 58 (about 680 ohms) is coupled between the wire 50 and the pin 20c, while a DC blocking capacitor 60 (about 1 $\mu$F) is coupled between the wire 50 and the pin 20d.

The second portion of the second unit means 14 comprises a differential operational amplifier 63, such as Type No. INA 101M, manufactured by Burr-Brown Corp., Tuscson, Ariz. Numbers in parenthesis are pin numbers thereof. The pins (1) and (4) are connected to a gain setting resistor 62 (about 39 ohms). The positive input signal pin (5) is connected to the pin 22d of the connector 18 and through a DC return resistor 64 (about 220K) to the pin 22b. The negative signal input pin (10) and the common pin (7) are connected to the grounded pin 22b. The positive and negative power pins (9) and (6) are coupled to the pins 22a and 22c, respectively, and also respectively receive positive and negative voltages of about +9 and −9 volts, respectively, through polarity protection diodes 66 and 68, respectively, from terminals 70 and 72, respectively, that are coupled to a dual voltage power supply or batteries (neither shown). A common connection for the power supply return is available at the terminal 74, which is connected to the pin 22b. The output signal pin (8) is coupled to an output connector 78 through a current limiting resistor 76 (about 1K). An output means, such as an oscilliscope or audio amplifier and loudspeaker (none shown), is connected to the output connector 78.

In operation, the first unit means is disposed proximate the subject with the antenna 34 proximate an artery, the connectors 16 and 18 are mated, the output means connected to the connector 78 and voltages applied to the terminals 70 and 72. These voltages are applied to the first unit means 11 via the wires 46, 48, and 50 so that the oscillator will commence oscillation. As an artery expands and contracts with each heart beat, the loading on the antenna 34 changes. In turn, this causes a change in the emitter current of the transistor 26, which causes a pulsating DC or baseband signal in accordance with the pulse rate to be conveyed by the wire 50 and applied through the capacitor 60 to the positive signal input pin (5). This signal is amplified by the amplifier 63 and can then be seen or heard on the output means.

It will be appreciated that since the first unit means 11 provides a pulsating DC output signal as opposed to an RF or microwave one, the length of the cable 12 is not critical and long lengths do not impair accuracy. Further, since the first unit means 11 comprises only an oscillator that provides a pulsating DC signal, and no other microwave components, it can be readily miniturized and fitted into a helmet.

The present invention is not limited to pulse monitoring at the STA. It can monitor at any artery, e.g., the radial, in which case it can determine blood pressure when used in conjunction with a pressure cuff.

What is claimed is:

1. Apparatus for monitoring the pulse rate of a subject, said apparatus comprising:

a first unit means having an oscillator adapted to be proximate said subject and drawing supply current in accordance with the subject loading thereon, said unit means providing a pulsating DC signal in accordance with the pulse rate of said subject;

a cable coupled to said first unit means to receive said pulsating DC signal and to convey a supply voltage to said first unit means; and a second unit means adapted to be placed distant from said subject and coupled to said cable for receiving and amplifying said pulsating DC signal and to provide said voltage to said cable and thus to said first unit means.

2. The apparatus of claim 1 wherein said cable comprises a shielded cable.

3. The apparatus of claim 1 wherein said second unit means provides power to said first unit means.

4. The apparatus of claim 1 wherein said second unit means comprises an operational amplifier.

5. The apparatus of claim 1 wherein said oscillator comprises a microwave oscillator.

6. The apparatus of claim 5 wherein said oscillator has a frequency of about 2450±50 MHz.

7. The apparatus of claim 1 wherein said oscillator comprises an antenna adapted to be disposed proximate said subject.

8. The apparatus of claim 4 wherein said antenna is adapted to be disposed proximate an artery of said subject.

* * * * *